(12) United States Patent
Nägele et al.

(10) Patent No.: US 6,433,861 B1
(45) Date of Patent: Aug. 13, 2002

(54) METHOD AND APPARATUS FOR A NON-INVASIVE MEASUREMENT OF THE VELOCITY OF A GAS OR A FLUID MEDIUM

(76) Inventors: Martin Nägele, Ausser der Schleifmühle 27, D-28203 Bremen; Wilfried Staude, Otto-Gildemeister-Strasse 25, D-28209 Bremen, both of (DE)

( * ) Notice: Subject to any disclaimer, the term of this patent is extended or adjusted under 35 U.S.C. 154(b) by 0 days.

(21) Appl. No.: 09/743,021
(22) PCT Filed: Jul. 5, 1999
(86) PCT No.: PCT/DE99/02123
§ 371 (c)(1), (2), (4) Date: Jun. 13, 2001
(87) PCT Pub. No.: WO00/03249
PCT Pub. Date: Jan. 20, 2000

(30) Foreign Application Priority Data

Jul. 4, 1998 (DE) .......................... 198 29 940

(51) Int. Cl.[7] .............. G01P 3/36; G01J 1/42; G01T 1/00; G01F 1/00; G01N 21/00; G01N 21/33; G01N 21/35
(52) U.S. Cl. .............. 356/28; 250/356.1; 250/393
(58) Field of Search ............. 356/277, 28.5; 250/393, 356.1

(56) References Cited

U.S. PATENT DOCUMENTS

| | | | |
|---|---|---|---|
| 3,795,448 A | * 3/1974 | Fletcher et al. | 356/28 |
| 4,228,353 A | * 10/1980 | Johnson | 250/356 |
| 4,483,614 A | * 11/1984 | Rogers | 356/28.5 |
| 4,649,426 A | * 3/1987 | Bolstad | 358/101 |
| 4,807,990 A | * 2/1989 | Keefer | 356/28.5 |
| 4,919,536 A | * 4/1990 | Komine | 356/28.5 |
| 4,988,190 A | * 1/1991 | Miles | 356/28 |
| 5,002,389 A | 3/1991 | Benser | |
| 5,025,160 A | * 6/1991 | Watt | 250/356.1 |
| 5,543,617 A | * 8/1996 | Roscoe et al. | 250/259 |
| 5,708,495 A | * 1/1998 | Pitz et al. | 356/28 |
| 5,982,478 A | * 11/1999 | Ainsworth et al. | 356/28 |

FOREIGN PATENT DOCUMENTS

EP 0 374 822 6/1990

OTHER PUBLICATIONS

"Air–Flow Visualization Using the Photoluminescence of Infrared–Sensitive Phosphor" *IBM Technical Disclosure Bulletin*, vol. 34, No. 2, Jul. 1991, pp. 48–49.
Abstract for Japanese 08278251, *Patent Abstracts of Japan*, vol. 1997, No. 2, Feb. 28, 1997.

* cited by examiner

Primary Examiner—Thomas H. Tarcza
Assistant Examiner—Brian Andrea
(74) Attorney, Agent, or Firm—Schiff Hardin & Waite

(57) ABSTRACT

A method for non-invasive measurement of the velocity of a medium selected from either a gas or a fluid at an examination location by boosting atoms and molecules of the medium into an excited atomic or molecular state with a focused first pulsed light beam in the investigation location, allowing the excited atoms and/or molecules to relax into a metastable state and then boosting the atoms and/or molecules in the metastable state into an excited atomic or molecular state with a second pulsed light beam that is weaker than the intensity of the first beam to transirradiate the investigation location and to produce a characteristic luminescence, detecting the characteristic luminescence of the selectively excited atoms and/or molecules and determining the coordinates of the investigation location and of the occurrence of the luminescence of a luminescent cloud in an image field and then calculating the velocity of the medium on the basis of the distance between the investigation location and the mid-point of the luminescent cloud in view of the time interval.

14 Claims, 1 Drawing Sheet

METHOD AND APPARATUS FOR A NON-INVASIVE MEASUREMENT OF THE VELOCITY OF A GAS OR A FLUID MEDIUM

The present invention is directed to a method and to an apparatus for a non-invasive measurement of the velocity of a gas or of a fluid at an investigation location.

The measurement of the flow velocity in gases and fluids at physically inaccessible locations represents an interesting task in broad fields of natural science and technology. The investigations of flow fields around and in technical systems thereby assists in acquiring important information for the optimization of these systems. In the field of investigating the atmosphere, too, the question regarding the flow velocity at physically inaccessible locations is very important. This information is a fundamental importance for the operating safety of the systems in the field of air travel and space travel.

Previously known optical measuring methods can be divided into two classes. The class of Doppler anemometers wherein light is elastically scattered into particles introduced in the medium (gas or fluid) to be investigated given too low a plurality of naturally occurring particles, therefore also referred to as invasive, i.e. no real excitation in the medium occurs, and the class of measuring methods wherein no additional particles are introduced, therefore referred to as non-invasive, wherein an excitation is generated in the medium and the following luminescence is interpreted. The direct interpretation of laser-induced luminescence for measuring velocities in gases is disclosed, for example, by U.S. Pat. Nos. 5,002,389 of T. Benser and 4,483,614 of T. Rogers. In the known methods, a laser pulse is utilized for the excitation of the gas. The typical decay times of the luminescence triggered in this way lie in the range of a few nano seconds through micro seconds. The measuring methods can thus only be conditionally employed for flows having a low velocity.

SUMMARY OF THE INVENTION

The invention is thus based on the object of making a method and an apparatus available with which low velocities of a gas over a fluid can also be measured.

This object is inventively achieved by a method for non-invasive measurement of the velocity of a gas or of a fluid at an investigation location, comprising the following steps:

a) Boosting atoms and/or molecules present in the gas or the fluid into an excited atomic or, respectively, molecular state with a first pulsed light beam of a light source focused in the investigation location;

b) Following a time interval $\Delta t$ that is selected of at least a size of the time period for the excited atoms and/or molecules to turn into metastable states due to relaxation, selective boosting of the atoms and/or molecules in the metastable states into an excited atomic or, respectively, molecular state with a second pulse light beam of the light source that is weaker in intensity compared to the first light beam and that transirradiates the investigation location and the suspected, momentary location of the spatial region containing the atoms and/or molecules, so that a characteristic luminescence is produced;

c) detecting the characteristic luminescence of the selectively excited atoms and/or molecules and determining the coordinates of the investigation location and of the occurrence of the luminescence (luminescent cloud) in an image field; and d) calculating the velocity v of the gas or fluid on the basis of the distance s between the investigation location and the mid-point of the luminescent cloud as well as of the time interval $\Delta t$ as follows:

$$v = s/\Delta t.$$

This object is also achieved by an apparatus of the species initially cited in that said apparatus comprises a light source for generating pulsed light beams;

a first means for focusing a first pulsed light beam of the light source in an investigation location;

a second means for projecting a second pulsed light beam of the light source into a spatial region following a time interval $\Delta t$;

a third means for detecting luminescence in the spatial region and determining the coordinates of the investigation location and of the occurrence of luminescence (luminescent cloud) in an image field; and a processing means connected to the third means for calculating the velocity of the gas or of the fluid on the basis of the distance s between the investigation location and the mid-point of the luminescent cloud as well as the time interval $\Delta t$.

In particular, it can thereby be provided that the direction of the velocity is calculated in addition. The velocity vector is thus obtained.

According to another particular embodiment of the invention, it can be provided that the density of the gas or of the fluid is identified on the basis of the intensity of the characteristic luminescence. The density is thereby proportional to the intensity of the luminescence.

It can also be provided that the characteristic luminescence is additionally temporally detected, and the density of the gas or of the fluid is determined on the basis of the time curve of the characteristic luminescence.

It can be provided according to another particular embodiment of the invention that the characteristic luminescence is additionally spectrally selectively detected and the relative concentrations of the participating atoms and/or molecules are identified on the basis of the relative intensities of the various luminescent spectral lines. Conclusions about the temperature and collisions with other molecules at the location of the excitation can also be drawn on the basis of a more exact analysis of the spectral distribution of the luminescence.

Preferably, the characteristic luminescence is only detected during a fixed time interval $\Delta t_1$ after the selective boost. This leads to an improvement of the signal-to-noise ratio.

According to another particular embodiment of the invention, it can be provided that the velocity of air is identified.

It can thereby be particularly provided that a plasma is briefly generated by the boosting according to Step a).

It can also thereby be provided that $N_2$ molecules are preferably boosted by the plasma generation and these relax into the metastable state $A^3\Sigma^+_u$ after a short time; further, in Step b) the $N_2$ molecules are boosted from the $A^3\Sigma^+_u$ state into the $B^3\Pi_g$ state; and, in Step c), the luminescence of the $B^3\Pi_g$ state is detected.

It can be provided in the apparatus that the third means comprises a camera.

It can also be provided that the camera is a CCD camera, potentially with image intensifier.

According to a particular embodiment of the apparatus, the third means comprises two PSDs (Position Sensitive Device) that are arranged crossed. In this case, the signal of the two detectors directly corresponds to the transversal coordinates of the luminescent cloud.

Finally, it can also be provided that the third means is spectrally selective.

The invention is based on the surprising perception that the division of the excitation process into two Steps a) and b) that can ensue in a time interval Δt that is greater than the typical decay times of the luminescence, velocity measurements can also be undertaken at moving gases or, respectively, fluids. This is possible because the metastable states comprise a life span in the range of milliseconds compared to the preceding luminescence time of 10 through a few 100 nanoseconds. The method can, in particular, be employed for measuring the air velocity in front of a flying aircraft, the turbulent wake around and behind an aircraft, of gas/fluid velocities having high topical resolution without influencing the flow conditions and of flow conditions at elements around which a gas or fluid flows with high topical resolution. Over and above, the inventive method, in a particular embodiment thereof, offers the possibility of additionally defining the density and/or composition at the medium at the investigation location.

Further features and advantages of the invention derive from the claims and from the following specification, wherein an exemplary embodiment is explained in detail on the basis of schematic drawings.

DESCRIPTION OF THE PREFERRED EMBODIMENTS

Figure 1:
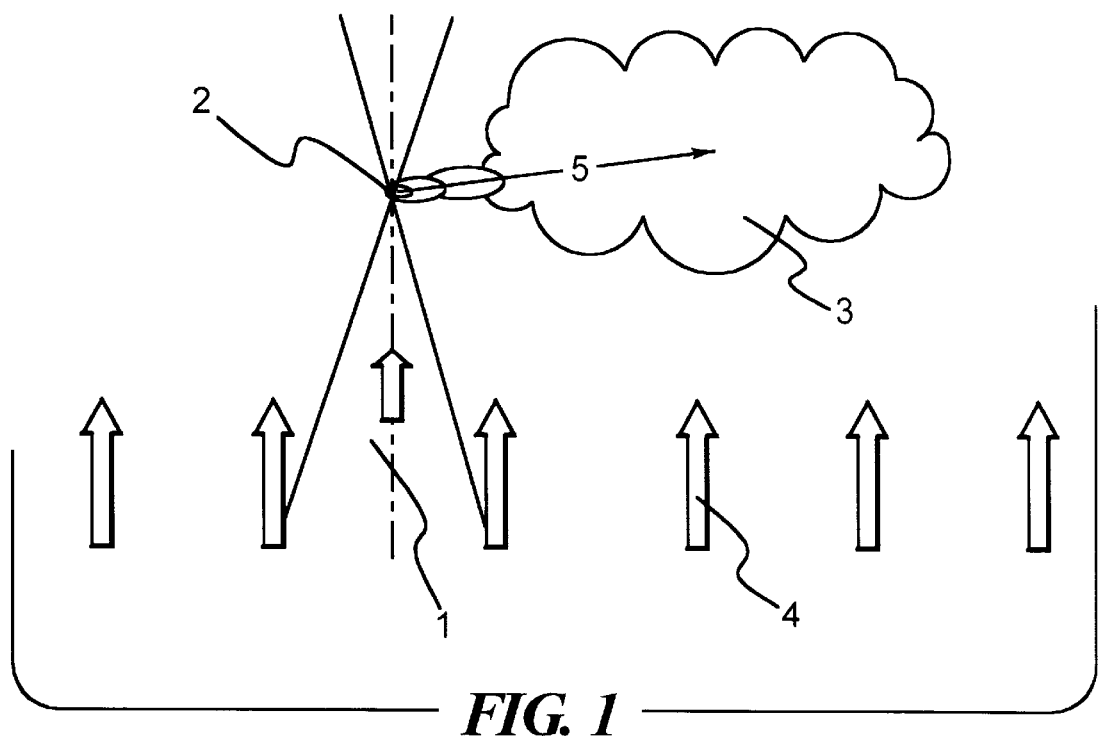
FIG. 1 schematically illustrates a luminescence of atoms and/or molecules (luminescent cloud) after excitation by a light source.
Figure 2:
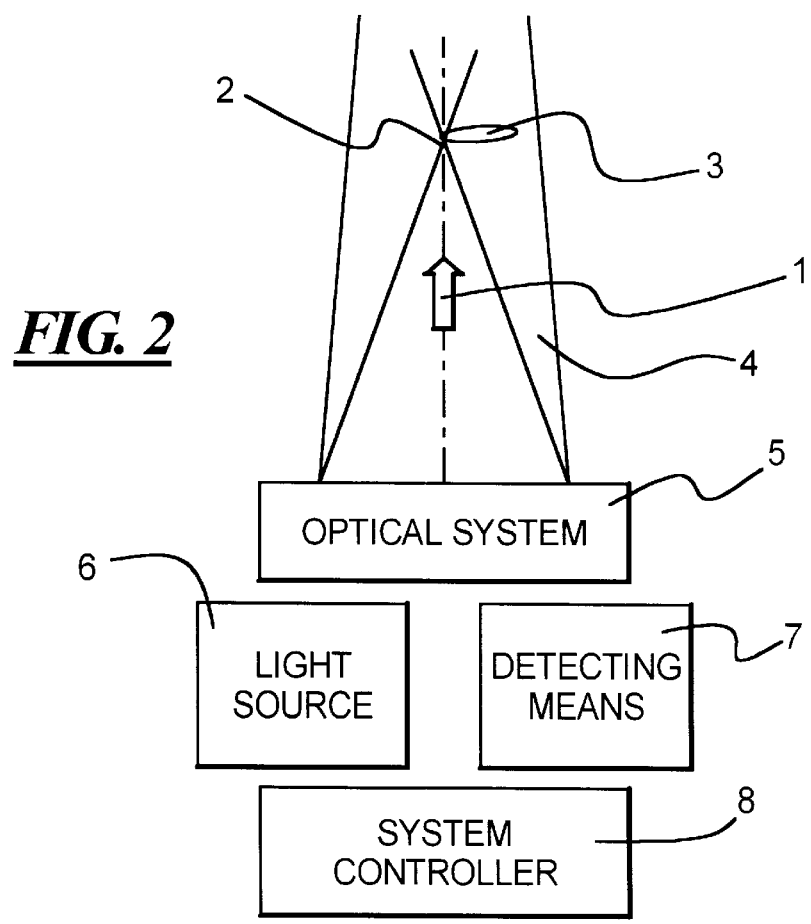
FIG. 2 schematically illustrates a specific embodiment of the inventive apparatus.

In FIG. 1, reference character 1 identifies a focused, first pulsed light beam. This focused light beam 1 derives from a light source 6 (FIG. 2) in the form of a laser whose exit beam is focused by a first means 5 in the form of an optical system, being focused in an investigation location 2 (also see FIG. 2). The same optical system also serves the purpose of generating a non-focused, second pulsed light beam 4 of the light source 6 and for the reception of luminescent light and forwarding thereof to a means 7 for detecting luminescence in the form of a camera (see FIG. 2). A system controller 8 serves the purpose of controlling the method sequences, i.e., in particular, the time sequence of the emission of the first and second pulsed light beams as well as the following detection of luminescence.

A central feature of the inventive method is the division of the excitation process into two steps that, each triggered by a (first or, respectively, second) pulsed light beam 1 and 4, follow one another variably in time. The topical resolution of the method derives from the sharply focused light beam 1 of the first laser pulse. The relatively high intensity that is thus achieved and that, in particular, can also lead to a brief-duration plasma generation, allows the excitation of the gas or, respectively, of the fluid such that atoms and/or molecules remain in metastable states after the immediately following relaxation cascade. These metastable states are typically achieved a few 10 through a few 100 nanoseconds after the first, exciting laser pulse of the first laser beam 1. The luminescence emitted in this process - in contrast to the above-described known method—is not evaluated further here, since the excited medium (gas or fluid) has only traversed a path of a few micrometers in 100 nanoseconds given a typical velocity of 10 m/s which cannot be interpreted with certainty from a greater distance. The remaining cloud of metastable states, also referred to as luminescent cloud 3, whose life span can lie in the range of a few milliseconds through seconds, is therefore interrogated with a second laser pulse of the second light beam 4 after a variable time interval Δt. This laser beam 4 is emitted temporally and spatially such that it still encounters an adequate density of metastable states and transirradiates the spatial region containing the suspected, momentary location for the atoms and/or molecules. When, for example, a time interval Δt of two milliseconds is set between the first (exciting) light beam 1 and the second (interrogating) light beam 4, the exemplary medium moves 20 mm further given 10 m/s, which can still be very easily mensurationally acquired even from greater distances.

The second (interrogating) light beam 4 selectively excites only the metastable states. Due to the following relaxation upon emission of luminescence, the region with metastable states (luminescent cloud 3) contrasts clearly from the background. This luminescent light is imaged by the first means 5 into the third means 7, where it is registered by an imaging system (camera). The imaging system can be optionally equipped with one or more spectrally selective elements or channels in order to enable a determination of the composition of the medium at the location of the excitation by interrogating different characteristic luminescent transitions of different molecules.

LIST OF REFERENCE CHARACTERS 1 focused light beam
2 investigation location
3 luminescent cloud
4 unfocused light beam
5 first and second means
6 light source
7 third means
8 system controller
s distance between investigation location and mid-point of the luminescent cloud
Δt Time interval
$\Delta t_1$ Time interval
v velocity

We claim:

1. A method for non-invasive measurement of the velocity of a medium selected from a gas or a fluid medium at an examination location, comprising the following steps:

boosting atoms and/or molecules present in the medium into an excited atomic or, respectively molecular state with a first pulsed light beam of a light source focused into a point at the investigation location to briefly generate a plasma;

following a time interval Δt that is selected of at least a size of a time period to allow the excited atoms and/or molecules of the plasma to relax into metastable states, selective boosting of the atoms and/or molecules in the metastable states into an excited atomic or, respectively, molecular state with a second pulse light beam of the light source that is weaker in intensity compared to the first light beam and that transirradiates the investigation location and the suspected, momentary location of the spatial region containing the atoms and/or molecules, so that a luminescent cloud of a characteristic luminescence is produced;

detecting the characteristic luminescence of the selectively excited atoms and/or molecules and determining the coordinates of the investigation location and of the occurrence of the luminescence in an image field; and calculating the velocity v of the medium on the basis of the distance s between the investigation location and the mid-point of the luminescent cloud as well as of the time interval Δt as follows:

$$v=s/\Delta t.$$

2. Method according to claim 1, the characteristic luminescence is additionally detected over time, and the density of the gas or of the fluid is identified on the basis of the time curve of the characteristic luminescence.

3. Method according to claim 1, the characteristic luminescence is additionally detected spectrally selectively, and the relative concentrations of the participating atoms and/or molecules are determined on the basis of the relative intensities of the various luminescent spectral lines.

4. Method according to claim 1, the characteristic luminescence is detected only during a fixed time interval $\Delta t_1$ after the selective boosting.

5. A method according to claim 1, wherein the step of calculating includes determining a direction of the velocity.

6. A method according to claim 1, which includes determining the density of the medium from the intensity of the characteristic luminescence.

7. A method according to claim 1, wherein the medium is air and the velocity of the air is calculated.

8. A method according to claim 7, wherein $N_2$ molecules are preferable boosted by the plasma generation, and these relax into the metastable state $A^3\Sigma^+_u$ after a brief time; during the selective boosting, the $N_2$ molecules are boosted from the $A^3\Sigma^+_u$ state into the $B^3\Pi_g$ state; and, during the step of detecting, the luminescence of the $B^3\Pi_g$ state is detected.

9. A method according to claim 1, wherein a laser is employed as the light source.

10. Apparatus for non-invasive measurement of a velocity of a medium selected from a gas and a fluid comprising:

a light source for generating a first pulsed light beam and a second pulsed light beam;

first means for focusing the first pulsed light beam of the light source into a point at an investigation location to generate a plasma;

second means for projecting the second pulsed light beam of the light source into a spatial region following a time interval;

third means for detecting luminescence in the spatial region and determining the coordinates of the investigation location and of the occurrence of luminescence of a luminescent cloud in an image field; and a processing means connected to the third means for calculating the velocity of the medium on the basis of the distance between the investigation location and the mid-point of the luminescent cloud as well as the time interval.

11. Apparatus according to claim 10, wherein the third means comprises a camera.

12. Apparatus according to claim 11, wherein the camera is a CCD camera, potentially with image intensifier.

13. An apparatus according to claim 10, wherein the third means comprises two position-sensitive devices arranged crossed.

14. An apparatus according to claim 10, wherein the third means is spectrally selected.

* * * * *